(12) United States Patent
Oyola et al.

(10) Patent No.: US 8,377,056 B2
(45) Date of Patent: Feb. 19, 2013

(54) METHOD OF TREATING TISSUE WITH RADIO FREQUENCY VASCULAR ELECTRODE ARRAY

(75) Inventors: Arnold E. Oyola, Northborough, MA (US); Erin McKenna, Boston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1822 days.

(21) Appl. No.: 11/564,813

(22) Filed: Nov. 29, 2006

(65) Prior Publication Data

US 2007/0167944 A1 Jul. 19, 2007

Related U.S. Application Data

(60) Provisional application No. 60/755,738, filed on Dec. 29, 2005.

(51) Int. Cl.
*A61B 18/12* (2006.01)
(52) U.S. Cl. .......................................................... 606/41
(58) Field of Classification Search .................... 606/28, 606/34, 41
See application file for complete search history.

(56) References Cited

U.S. PATENT DOCUMENTS

| | | | |
|---|---|---|---|
| 5,919,187 A | 7/1999 | Guglielmi et al. | |
| 6,379,353 B1 | 4/2002 | Nichols | |
| 6,423,056 B1 * | 7/2002 | Ishikawa et al. | 606/28 |
| 6,958,061 B2 * | 10/2005 | Truckai et al. | 606/28 |
| 2002/0151886 A1 | 10/2002 | Wood | |
| 2004/0098030 A1 | 5/2004 | Makower et al. | |

FOREIGN PATENT DOCUMENTS

| | | |
|---|---|---|
| WO | WO9629946 | 10/1996 |
| WO | WO 2005/110261 A2 | 11/2005 |

OTHER PUBLICATIONS

Extended European Search Report for EP Patent Application No. 06127097.1, dated May 7, 2007, Applicant: Boston Scientific Scimed, Inc. (6 pages).

* cited by examiner

*Primary Examiner* — Michael Peffley
*Assistant Examiner* — Daniel Fowler
(74) *Attorney, Agent, or Firm* — Vista IP Law Group LLP

(57) ABSTRACT

A method of treating a patient is provided. The method comprises delivering an electrically conductive material within a vascular network, wherein the electrically conductive material embolizes in a region of the vascular network to form a vascular electrode array that assumes a geometry of the embolized region of the vascular network. The method may optionally comprise delivering a containment agent within the vascular network proximal to the delivered electrically conductive material to stabilize the vascular electrode array. The method further comprises applying electrical energy (e.g., radio frequency (RF) energy) to the vascular electrode array to therapeutically conduct electrical energy into a region of the targeted tissue adjacent the embolized region of the vascular network.

16 Claims, 11 Drawing Sheets

METHOD OF TREATING TISSUE WITH RADIO FREQUENCY VASCULAR ELECTRODE ARRAY

CROSS REFERENCE TO RELATED APPLICATION

The present application claims benefit of provisional application U.S. Ser. No. 60/755,738, filed Dec. 29, 2005, the entire disclosure of which is hereby incorporated by reference herein.

FIELD OF THE INVENTION

The field of the invention relates generally to the treatment of solid tissue, e.g., tumors, using radio frequency (RF) ablation energy.

BACKGROUND OF THE INVENTION

The delivery of radio frequency (RF) energy to target regions within solid tissue is known for a variety of purposes of particular interest to the present inventions. In one particular application, RF energy may be delivered to diseased regions (e.g., tumors) in targeted tissue for the purpose of tissue necrosis. RF ablation of tumors is currently performed within one of two core technologies.

The first technology uses a single needle electrode, which when attached to a RF generator, emits RF energy from the exposed, uninsulated portion of the electrode. This energy translates into ion agitation, which is converted into heat and induces cellular death via coagulation necrosis. The second technology utilizes multiple needle electrodes, which have been designed for the treatment and necrosis of tumors in the liver and other solid tissues. PCT application WO 96/29946 and U.S. Pat. No. 6,379,353 disclose such probes. In U.S. Pat. No. 6,379,353, a probe system comprises a cannula having a needle electrode array reciprocatably mounted therein. The individual electrodes within the array have spring memory, so that they assume a radially outward, arcuate configuration as they are advanced distally from the cannula.

In theory, RF ablation can be used to sculpt precisely the volume of necrosis to match the extent of the tumor. By varying the power output and the type of electrical waveform, it is possible to control the extent of heating, and thus, the resulting ablation. However, the size of tissue coagulation created from a single electrode, and to a lesser extent a multiple electrode array, has been limited by heat dispersion. As a consequence, when ablating lesions that are larger than the capability of the above-mentioned devices, the common practice is to stack ablations (i.e., perform multiple ablations) within a given area. This requires multiple electrode placements and ablations facilitated by the use of ultrasound imaging to visualize the electrode in relation to the targeted tissue. Because of the echogenic cloud created by the ablated tissue, however, this process often becomes difficult to accurately perform. This process considerably increases treatment duration and patent discomfort and requires significant skill for meticulous precision of probe placement.

In response to this, the marketplace has attempted to create larger lesions with a single probe insertion. Increasing generator output, however, has been generally unsuccessful for increasing lesion diameter, because an increased wattage is associated with a local increase of temperature to more than 100° C., which induces tissue vaporization and charring. This then increases local tissue impedance, limiting RF deposition, and therefore heat diffusion and associated coagulation necrosis. In addition, patient tolerance appears to be at the maximum using currently available 200 W generators.

It has been shown that the introduction of conductive fluid, such as saline, into the extra-cellular spaces of the targeted tissue increases the tissue conductivity, thereby creating a larger lesion size. However, because electrically conductive fluid may preferentially travel into fissures or spaces inside, and even outside, of the targeted tissue, application of ablation energy to the targeted tissue may result in irregular ablation shapes that may include healthy tissue.

For this reason, it would be desirable to provide improved electrosurgical methods and systems for more efficiently and effectively ablating tumors in the liver and other body organs that are larger than the single ablation capability of the electrode or electrode array on the electrosurgical device being used.

SUMMARY OF THE INVENTION

In accordance with the present inventions, a method of treating a patient is provided. The method comprises delivering an electrically conductive material within a vascular network, wherein the electrically conductive material embolizes in a region of the vascular network. The vascular network may be, e.g., a network of blood vessels, although the vascular network can be any physiological network in a patent through which fluid (liquid or air) flows. The embolic material may have a viscosity that, when introduced into the vascular network, allows the embolic material to naturally flow through the vascular network. The vascular network may comprise vessels that reduce in size at a periphery of the targeted tissue, and the electrically conductive material may comprise particles, each of which is sized to lodge within a vessel at the periphery of the targeted tissue. In one method, the electrically conductive material comprises embolic particles suspended within an electrically conductive solution. In another method, the electrically conductive material comprises embolic particles doped with metallic sub-particles.

The embolic material forms a vascular electrode array that assumes a geometry of the embolized region of the vascular network. The vascular electrode array may comprise a main shaft (e.g., corresponding to a main trunk of the vascular network) and an array of tines extending from the main shaft (e.g., corresponding to vessels extending from the main trunk). The method may optionally comprise delivering a containment agent within the vascular network proximal to the delivered electrically conductive material to stabilize the vascular electrode array.

The method further comprises applying electrical energy (e.g., radio frequency (RF) energy) to the vascular electrode array to therapeutically conduct electrical energy into a region of the targeted tissue adjacent the embolized region of the vascular network. In one method, the electrical energy therapeutically ablates the targeted tissue. The embolic material may have a viscosity that, when the electrical energy is applied, prevents the vascular network from closing. In this manner, electrical disconnects within the vascular electrode array are prevented or minimized. The embolized region of the vascular network may comprise the entirety of the vascular network, and the adjacent region of the targeted tissue may comprise the entirety of the targeted tissue, although less than the entirety of the vascular network may be embolized, and less than the targeted tissue can be exposed to the electrical energy. In one method, the electrically conductive material is introduced into the vascular network and the electrical energy is applied to the vascular electrode array via a single probe, although separate probes may be used to perform the respective functions.

In an optional method, the embolic material may be biologically non-resorbable, so that the vascular electrode array is permanent or semi-permanent. In this case, the method may further comprise applying additional electrical energy to the vascular electrode array, whereby the additional electrical energy is therapeutically conducted into any anomalies in the corresponding region of targeted tissue region that have occurred after the previous application of electrical energy.

In one method, targeted tissue external to the vascular network is treated. The vascular network is contoured to the general shape and size of the targeted tissue is provided, in which case, the vascular electrode array formed by the embolic material is likewise contoured to the general shape and size of the targeted tissue. Thus, it can be appreciated the electrical energy applied to the vascular electrode array is efficiently and effectively conveyed into the targeted tissue. This method lends itself well to the treatment of tumors, which are typically highly vascularized. In another method, an abnormality within the vascular network is treated. The abnormality may be, e.g., a hemorrhage or some other vascular abnormality, such as an Arterio Vascular Malformation (AVM), Arterio Vascular Fistula (AVF), Venous Malformation (VM), or Lymphatic Malformation (LM).

In another method, an electrically conductive material, which need not be embolic in nature, is delivered. The electrically conductive material has a viscosity that, when introduced into the vascular network, allows the electrically conductive material to naturally flow through the vascular network. In this case, the method further comprises delivering a containment agent within the vascular network proximal to the delivered electrically conductive material to stabilize the electrically conductive material, thereby forming a vascular electrode array that assumes a geometry of the vascular network. Electrical energy is then applied to the vascular electrode array to therapeutically conduct electrical energy into the vascular network.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE ILLUSTRATED SYSTEMS AND METHODS

Figure 1:
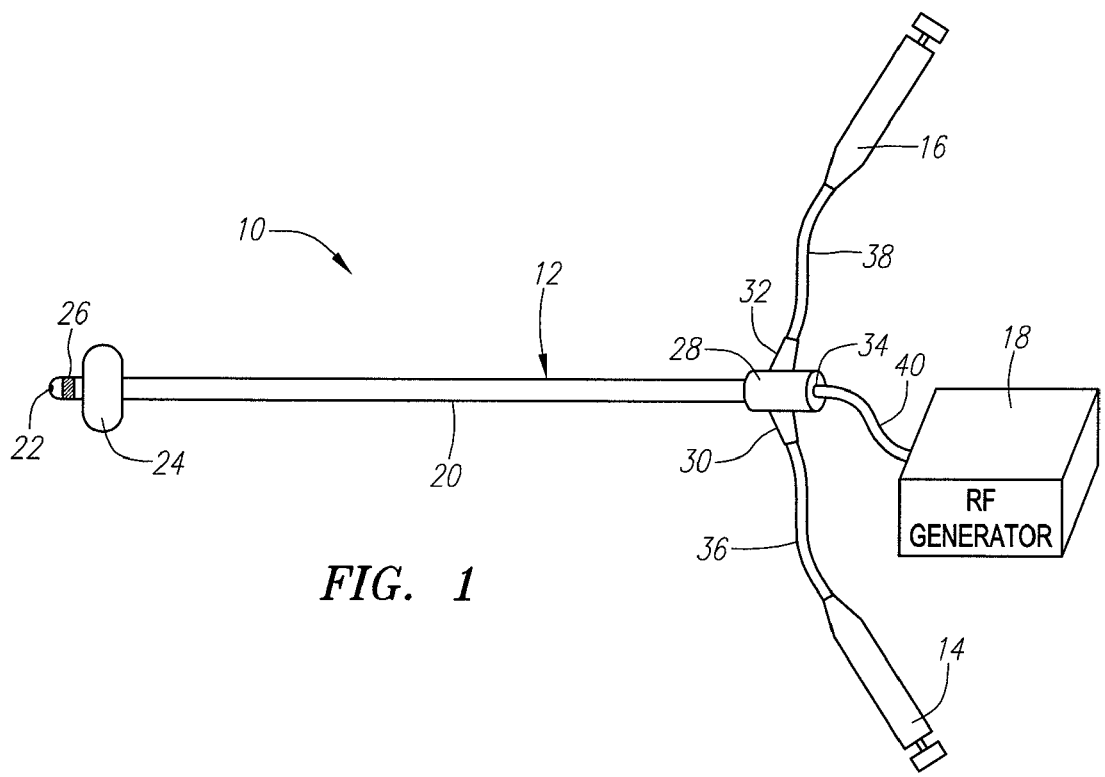
FIG. 1 is a perspective view of tissue treatment system constructed in accordance with a preferred embodiment of the present inventions.

Referring to FIG. 1, one embodiment of a tissue treatment system 10 constructed in accordance with the present inventions will now be described. The tissue treatment system 10 generally comprises an intravascular treatment catheter 12, a source of an electrically conductive embolic material 14, a source of inflation medium 16, and a source of ablation energy, and in particular, a radio frequency (RF) generator 18. As will be described in further detail below, the tissue treatment system 10 may be operated to deliver an electrically conductive material within a vascular network. The vascular network may be, e.g., a network of blood vessels. The electrically conductive material is designed to embolize the vascular network or at least a region thereof, which can then be stabilized to form a vascular electrode array. This vascular electrode array can then be energized with electrical energy, e.g., radio frequency (RF) energy, to treat tissue adjacent the vascular network, e.g., a tumor, or even to treat the vascular network itself.

The catheter 12 comprises an elongated flexible shaft 20 that can be conveniently delivered to a target region via the vasculature of a patient. The catheter 12 further comprises an embolic material delivery port 22 located at the distal tip of the catheter shaft 20, an inflatable balloon 24 mounted to the distal end of the catheter shaft 20, and a radio frequency (RF) electrode 26 suitably mounted to the distal end of the catheter shaft 20 between the embolic material delivery port 22 and balloon 24. The catheter 12 also comprises a handle 28 suitably mounted to the proximal end of the catheter shaft 20, and an embolic material entry port 30, balloon inflation port 32, and electrical connector 34 located on the handle 28. The embolic material entry port 30 and balloon inflation port 32 are fluidly coupled to the respective embolic delivery port 22 and balloon 24 via lumens (not shown) extending through the catheter shaft 20. The electrical connector 34 is electrically coupled to the electrode 26 via a radio frequency (RF) wire (not shown) extending through the catheter shaft 20.

The embolic material source 14 is mated to the embolic entry port 30 on the handle 28 via a tube 36, so that embolic material can be delivered from the source 14 out through the delivery port 22 into a vessel of the vascular network in which the distal end of the catheter shaft 20 resides. In the illustrated embodiment, the embolic material source 14 comprises a standard syringe filled with the embolic material. Alternatively, a pump or other suitable mechanism for conveying embolic material under positive pressure can be used.

The embolic material has an initial viscosity that allows the embolic material to easily flow through the vascular network in which the embolic material is intended to be delivered. At the time that the embolic material is stabilized into a vascular electrode array, the viscosity of the embolic material may increase depending on the treatment. For example, in certain treatments, it is preferable to design the embolic material, such that it hardens over a period of time, whereas there may be other treatments in which it is preferable to design the embolic material, such that it maintains a relatively low viscosity over time.

In the illustrated embodiment, the embolic material contains non-electrically conductive solid particles, such as microspheres or polyvinyl acetate (PVA) strings, that are capable of lodging within small vessels of the vascular network. As briefly stated above, the embolic material, as a whole, is electrically conductive, which for the purposes of this specification, means that the embolic material has a resistivity substantially lower than that of tissue, such as blood, so that electrical energy applied to the delivered embolic material preferentially uses the embolic material as a conductive path compared to the tissue that surrounds the embolic material. To this end, the embolic material comprises a highly electrically conductive solution, such as, e.g., calcium chloride, sodium chloride, etc., in which the embolic particles are suspended.

In optional embodiments, the electrically non-conductive embolic particles may be doped with metallic sub-particles, such as iron, silver, gold, etc., to render the embolic particles themselves electrically conductive. Or, instead of using embolic particles, electrically conductive devices, such as embolic coils, can be used. In either case, a solution, whether electrically conductive or not, is used to suspend, and therefore allow, the embolic particles or devices to easily flow through the vascular network in the presence of relatively small pressures.

In other optional embodiments, the embolic material, (i.e., the combination of the embolic particles and solution) is configured to harden in response to certain conditions, e.g., passage of time, temperature, and/or pH of environment. In these cases, it is possible that a containment mechanism, such as the balloon 24 is not needed, depending on the time that it takes for the embolic material to harden. As an example, the embolic material may take the form of a polymerizing or phase transition liquid that contains electrically conductive particles (e.g., ferritic, silver, gold, etc.) and that hardens or sets in response to these conditions. Or an electrically conductive fibrin sealant, such as Tisseel®, may be used as the embolic material. In other optional embodiments, the embolic material may be non-resorbable, so that the resulting vascular electrode array is permanent or semi-permanent. Suitable non-resorbable embolic materials include polyvinyl alcohol and cyanoacrylates. As will be described in further detail below, this allows subsequent treatments to be rendered. Any of the above-mentioned embolic materials may be enhanced with contrast agents and/or echogenic particles that would allow visualization of the embolic material using common imaging technologies, such as a fluoroscope or ultrasound imager.

In the illustrated embodiment, the single source 14 contains the embolic material. However, if the electrically conductive embolic material is designed to be formed by the mixing of separate components within the vascular network (e.g., embolic particles suspended within an electrically conductive solution, or the separate components of a tissue sealant), the components can be separately delivered from the distal end of the catheter shaft 20 where it naturally combines within the blood vessel to form the electrically conductive embolic material. In this case, two separate sources can be used to separately contain the components, in which case, an additional entry port, lumen, and delivery port (all not shown) will need to be incorporated into the catheter 12. Alternatively, the same source can be used to contain the components at different times. For example, the source 14 can be used to deliver one component via the delivery port 22, and then a second component via the same delivery port 22.

The inflation medium source 16 is mated to the balloon inflation port 32 on the handle 28 via a tube 38, so that inflation medium (e.g., saline) can be delivered from the source 16 into the interior of the balloon 24, thereby expanding the balloon 24 within the vessel of the vascular network in which the distal end of the catheter shaft 20 resides. In the illustrated embodiment, the inflation medium source 16 comprises a standard syringe filled within the inflation medium. Alternatively, a pump or other suitable mechanism for conveying the inflation medium under positive pressure can be used. As will be described in further detail below, inflation of the balloon 24 within the vessel effectively contains the embolic material within the region of the vascular network that is distal to the inflated balloon 24. In this manner, the electrically conductive embolic material becomes stabilized, thereby transforming it into a vascular electrode array. Inflation of the balloon 24 may also prevent or minimize the dilution of the electrically conductive embolic material, which may otherwise occur if blood was allowed to flow into the region of the vascular network occupied by the embolic material.

In alternative embodiments, instead of, or in addition to, using a balloon, other mechanisms can be used to contain the embolic material. For example, a powdered gelfoam mixed in a solution, such as saline and/or contrast agent, large PVA spheres, coils that induce thrombus formation, or a polymerizing or phase transition material that hardens/sets in response to certain conditions, can be delivered into the vascular network proximal to the embolic material. In this case, a separate source of the containment agent, delivery port, lumen, and entry port can be provided on the catheter 12. Alternatively, the mechanism used to deliver the electrically conductive embolic material can be used to subsequently deliver the containment agent.

The RF generator 18 is mated to the electrical connector 34 on the handle 28 via a RF cable 40, so that RF energy can be delivered from the RF generator 18 to the electrode 26. The RF generator 18 may be a conventional RF power supply that operates at a frequency in the range from 200 kHz to 9.5 MHz, with a conventional sinusoidal or non-sinusoidal wave form. In the illustrated embodiment, the RF current is delivered to the electrode 26 in a monopolar fashion, which means that current will pass from the electrode 26, which is configured to concentrate the energy flux in order to have an injurious effect on the surrounding tissue, and a dispersive electrode (not shown), which is located remotely from the electrode 26 and has a sufficiently large area (typically 130 cm$^2$ for an adult), so that the current density is low and non-injurious to surrounding tissue. In the illustrated embodiment, the dispersive electrode may be attached externally to the patient, e.g., using a contact pad placed on the patient's flank. Alternatively, the RF current is delivered to the electrode 26 in a bipolar fashion, which means that current will pass from the electrode 26 to another electrode within the patient's body.

While the mechanisms for delivering and containing the electrically conductive embolic material within a vascular network, and applying RF ablation energy to the resulting vascular electrode array are implemented in a single intravascular catheter, as illustrated in FIG. 1, it should be appreciated that the mechanisms can be implemented in separate catheters. For example, one catheter can be used to deliver and contain the embolic material, and another catheter can be used to apply RF ablation energy to the resulting vascular electrode array. Also, such mechanisms can be implemented in one or more rigid probes that can be percutaneously introduced through the patient's skin directly into the treatment region for delivery and containment of the embolic material and application of RF energy.

Figure 2:
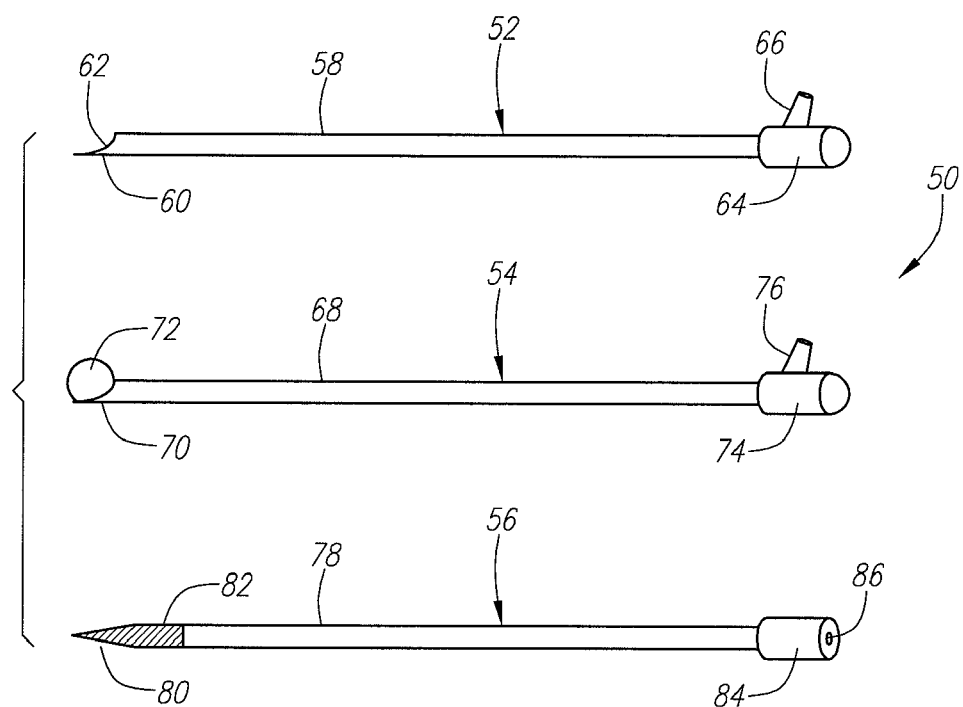
FIG. 2 is a perspective view of a tissue treatment kit arranged in accordance with a preferred embodiment of the present inventions.

For example, referring to FIG. 2, a tissue treatment kit 50 constructed in accordance with the present inventions will now be described. The tissue treatment kit 50 is configured for percutaneously treating a patient, and generally comprises a separate embolic material delivery probe 52, vessel occlusion probe 54, and tissue ablation probe 56.

The embolic material delivery probe 52 comprises an elongated shaft 58 composed of a rigid or semi-rigid material, such that the probe 52 can be introduced through solid tissue to the targeted tissue. The probe 52 may optionally be introduced to the targeted tissue via a cannula (not shown). To facilitate introduction through solid tissue, the distal end of the probe shaft 58 has an open tissue-penetrating tip 60. The embolic material delivery probe 52 also comprises an embolic material delivery port 62 located at the distal tip of the probe shaft 58 and a delivery lumen (not shown) extending through the probe shaft 58 in fluid communication with the delivery port 62. The embolic material delivery probe 52 further comprises a handle 64 mounted to the proximal end of the probe shaft 58, and an embolic material entry port 66 disposed on the handle 64 for mating with the embolic material source 14 (shown in FIG. 1). In the same manner described above, embolic material can be conveyed from the source 14 out through the delivery port 62 at the distal end of the probe shaft 58. The embolic material may be any one or more of the varying compositions described above.

The vessel occlusion probe 54 comprises an elongated shaft 68 composed of a rigid or semi-rigid material, such that the probe 54 can be introduced through solid tissue to the targeted tissue. The probe 54 may optionally be introduced to the targeted tissue via a cannula (not shown). To facilitate introduction through solid tissue, the distal end of the probe shaft 68 has an open tissue-penetrating tip 70. The vessel occlusion probe 54 also comprises a balloon 72 located at the distal tip of the probe shaft 68 and a delivery lumen (not shown) extending through the probe shaft 68 in fluid communication with the interior of the balloon 72. The vessel occlusion probe 54 further comprises a handle 74 mounted to the proximal end of the probe shaft 68, and an inflation medium entry port 76 disposed on the handle 74 for mating with the inflation medium source 16 (shown in FIG. 1). In the same manner described above, inflation medium can be conveyed from the source 16 to inflate the balloon 72 at the distal end of the probe shaft 68. Alternatively, rather than using the balloon 72 or in addition to the balloon 72, vessel occlusive materials, such as any one or more of the containment agents described above, can be delivered through a lumen (not shown) within the vessel occlusion probe 54.

In the illustrated embodiment, the tissue ablation probe 56 takes the form of a single-needle ablation probe. The ablation probe 56 comprises an elongated shaft 78 composed of a rigid or semi-rigid material, such that the probe 56 can be introduced through solid tissue to the targeted tissue. The probe 56 may optionally be introduced to the targeted tissue via a cannula (not shown). To facilitate introduction through solid tissue, the distal end of the probe shaft 78 has a closed tissue-penetrating tip 80. The ablation probe 56 further comprises an electrode 82 carried by the distal end of the probe shaft 78. In the illustrated embodiment, the probe shaft 78 is composed of an electrically conductive material, such as stainless steel, and an electrically insulative coating can be applied to the probe shaft 78, in which case, an uninsulated portion of the probe shaft 78 can form the electrode 82. Alternatively, the probe shaft 78 may be composed of an electrically insulative material, and the distal end of the probe shaft 78 can be coated with an electrically conductive material to form the electrode 82. The ablation probe 78 further comprises a handle 84 mounted to the proximal end of the probe shaft 78, and an electrical connector 86 disposed within the handle 84 for electrically coupling to the RF generator 18 (shown in FIG. 1). In the same manner described above, RF energy can be conveyed from the RF generator 18 to the electrode 82 in a monopolar arrangement, although such RF energy can be alternatively conveyed in a bipolar arrangement. In alternative embodiments, ablation probes with deployable needle electrodes may be used, although, to a certain extent, the use of a vascular electrode array to ablate the targeted tissue obviates the need to use a multi-electrode ablation probe.

One method of treating targeted tissue, and in particular, a tumor, will now be described. The targeted tissue may be located anywhere in the body where hyperthermic exposure may be beneficial. Most commonly, the targeted tissue will comprise a solid tumor within an organ of the body, such as the liver, kidney, pancreas, breast, prostrate (not accessed via the urethra), and the like. The volume to be treated will depend on the size of the tumor or other lesion, typically having a total volume from 1 $cm^3$ to 150 $cm^3$, and often from 2 $cm^3$ to 50 $cm^3$ The peripheral dimensions of the treatment region will usually be regular, e.g., spherical or ellipsoidal, but will more usually be irregular. The treatment region may be identified using conventional imaging techniques capable of elucidating a targeted tissue, e.g., tumor tissue, such as ultrasonic scanning, magnetic resonance imaging (MRI), computer-assisted tomography (CAT), fluoroscopy, nuclear scanning (using radiolabeled tumor-specific probes), and the like. Preferred is the use of high resolution ultrasound of the tumor or other lesion being treated, either intraoperatively or externally.

Figure 3A:
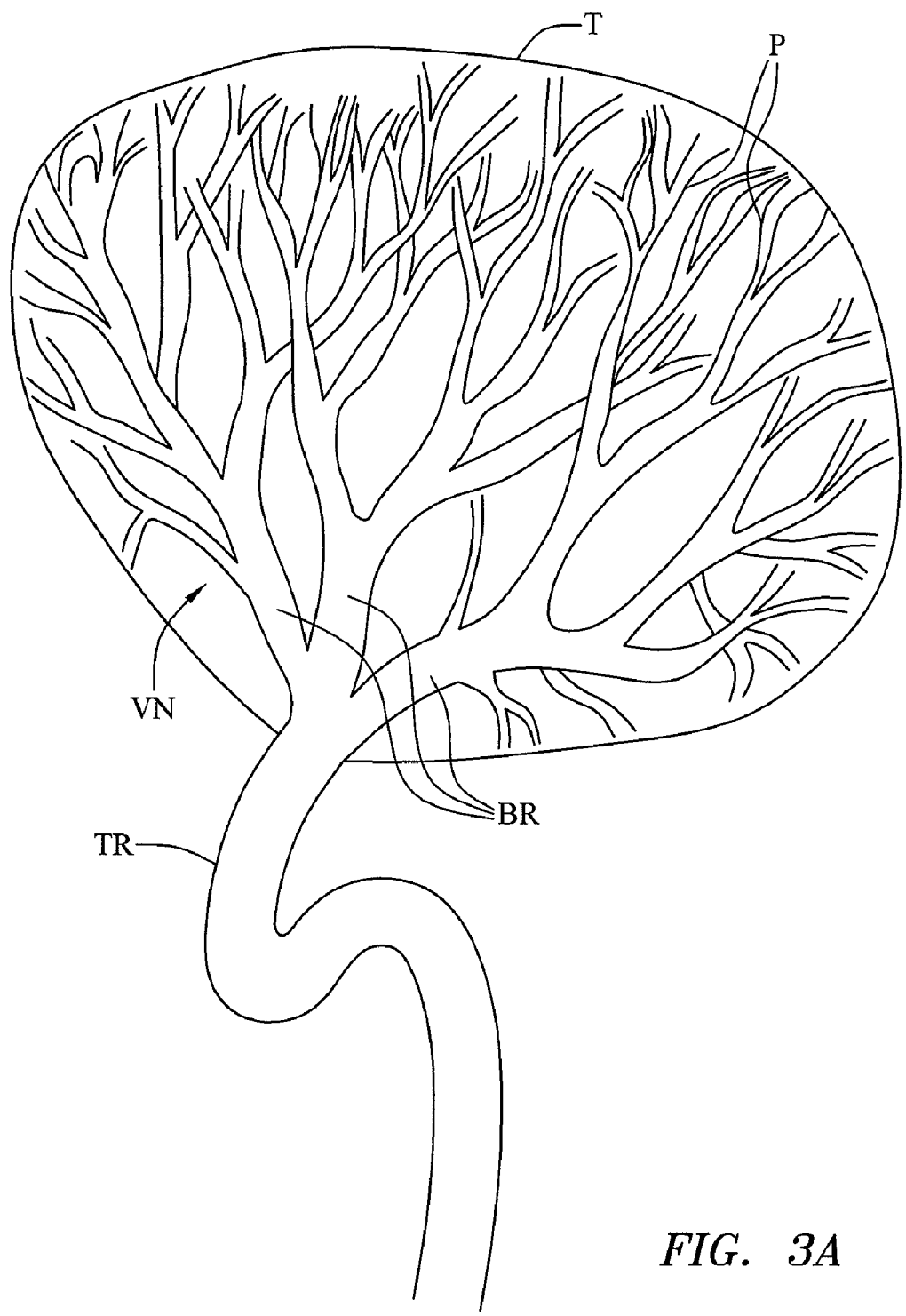
FIGS. 3A-3F illustrate views of one preferred method of using the tissue treatment system of FIG. 1 to treat a vascularized tumor.

Referring to FIGS. 3A-3F, a method of treating a tumor with the tissue treatment system 10 illustrated in FIG. 1 will now be described. In the method specifically illustrated, the targeted tissue takes the form of a tumor T with an associated network of blood vessels VN that supplies blood to nourish the tumor T (FIG. 3A). As shown, the network VN comprises a main trunk TR with smaller vessel branches BR (e.g., arteries), which lead to even smaller peripheral vessels P (e.g., arterioles and capillaries). Significantly, because tumors are highly vascularized, the vessel network VN is physically contoured to the general shape and size of the tumor T. The treatment method takes advantage of this to create a vascular electrode array that is also physiologically contoured to the shape and size of the tumor T. As will be discussed in further detail, the vascular electrode array can be energized, i.e., ablation energy can be applied to the electrode array, which is then distributed to the surrounding tumor, resulting in the effective and efficient ablation of the tumor T.

Figure 3B:
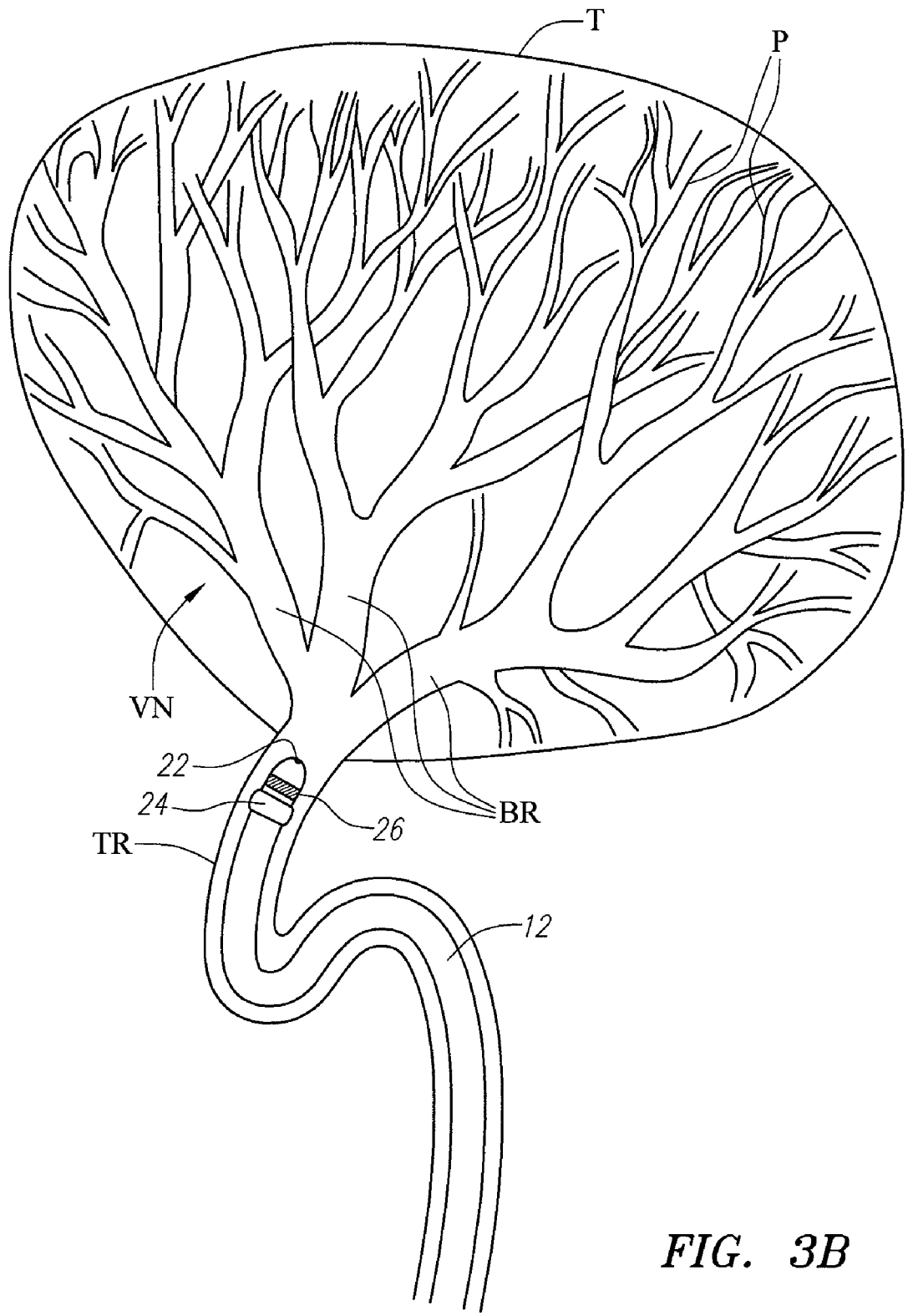

To create the vascular electrode array, the catheter 12 is first conventionally introduced though the vasculature of the patient from an entry point (e.g., a puncture within the femoral artery) until the distal end of the catheter 12 resides within the vessel network VN or proximal thereto (FIG. 3B). In the illustrated embodiment, the distal end of the catheter 12 is located within the main trunk TR of the vessel network VN, which supplies the remaining vessels of the network VN with blood.

Figure 3C:
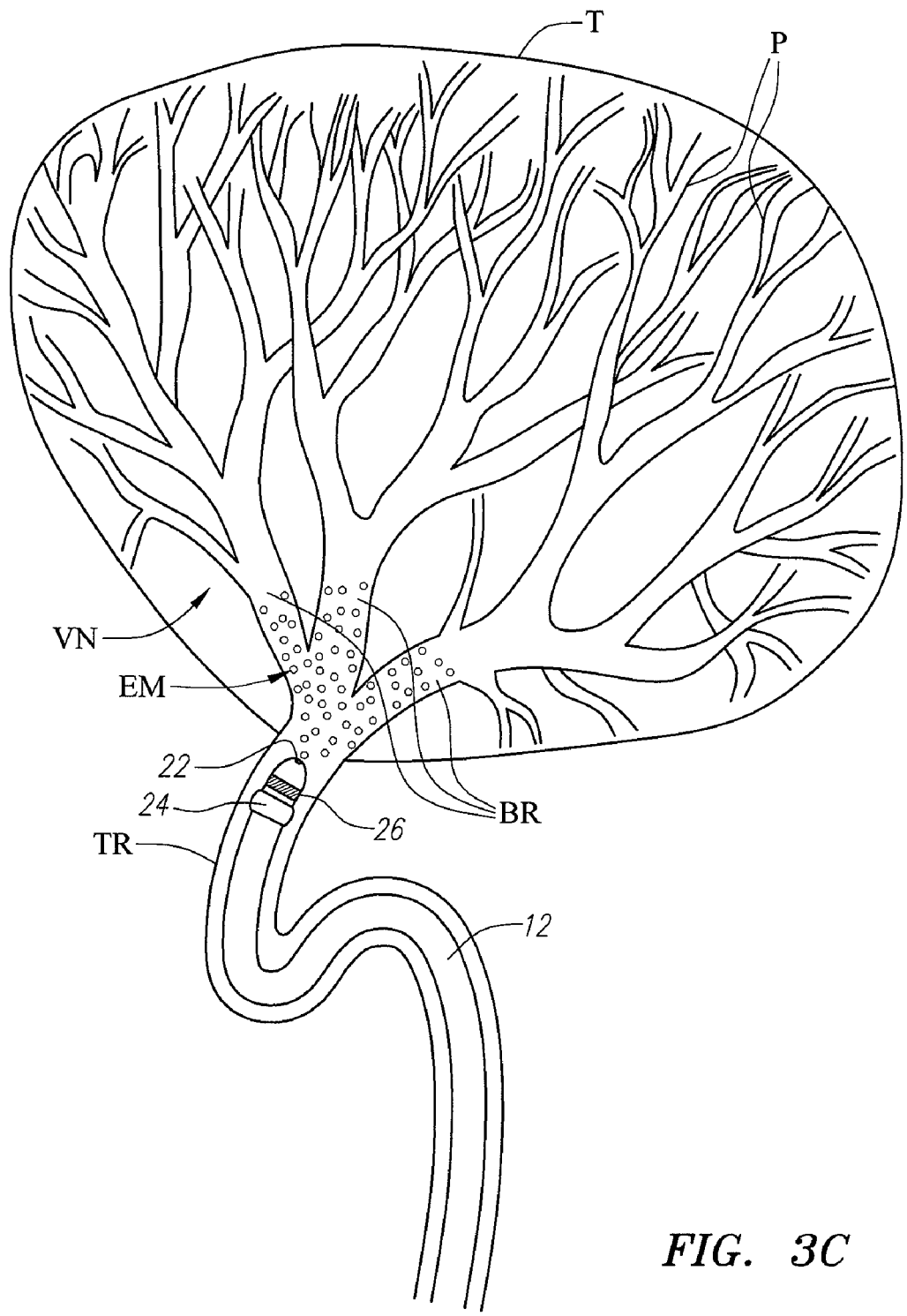
Figure 3D:
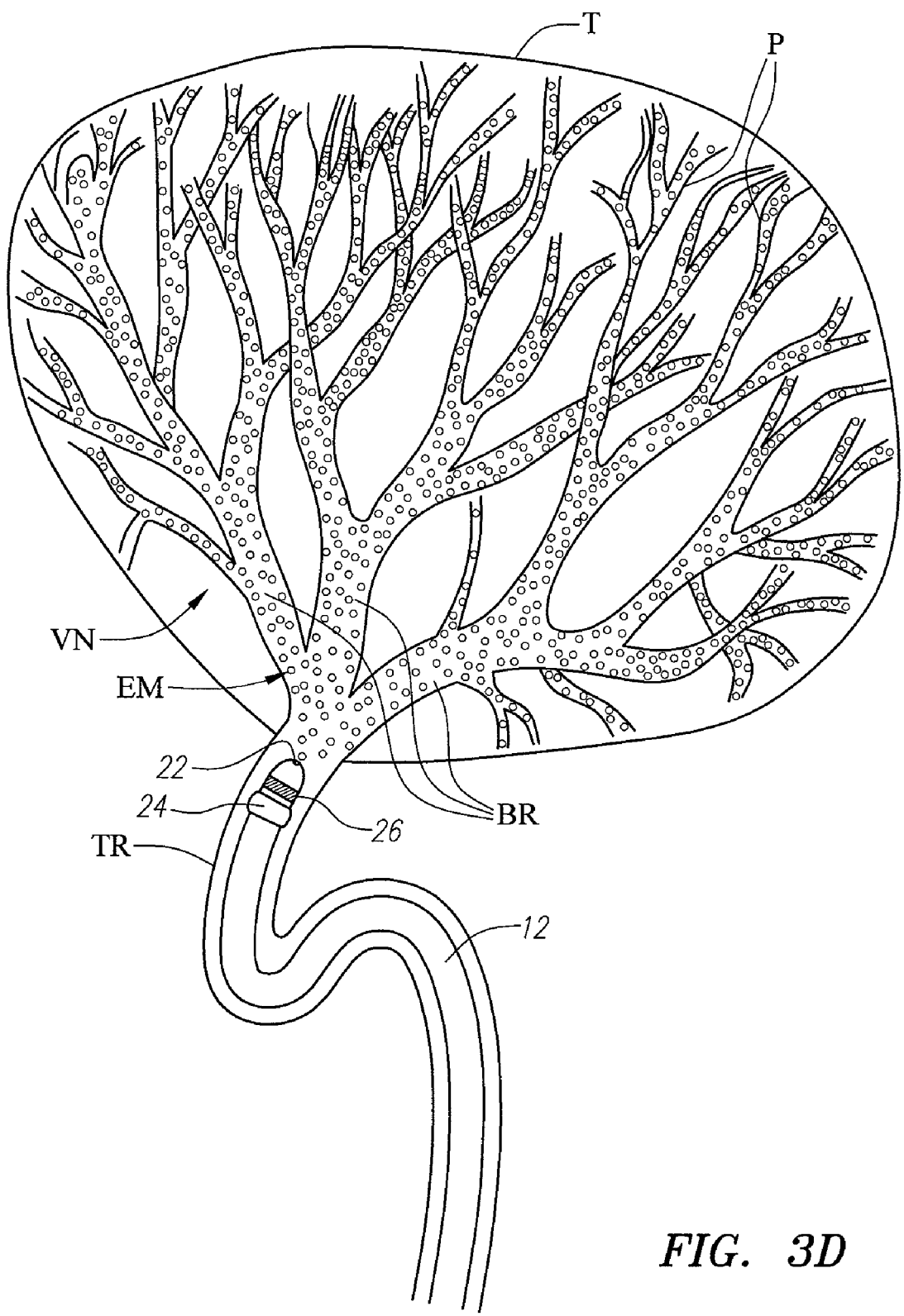

Next, the electrically conductive embolic material EM is delivered from the embolic material source 14 (shown in FIG. 1) through the catheter 12 and out of the delivery port 22 into the trunk TR of the vessel network VN, where it is conveyed into the vessel branches BR and smaller peripheral vessels P (FIG. 3C). The blood flow facilitates the perfusion of the embolic material EM throughout the vessel network VN. The solid particles suspended within the solution of the embolic material EM will flow into and lodge within the smaller peripheral vessels P, thereby allowing proximal branch BR vessels and trunk T to fill with the embolic material EM (FIG. 3D). In an alternative method, the electrically conductive solution in which the solid particles are suspended may be delivered prior or subsequent to the delivery of the solid embolic particles, which then combine within the vessel network VN to form the electrically conductive embolic material EM. From this, it can be appreciated that the selection of an arterial network for distribution of the embolic material EM is superior, since the embolic material can be introduced into a single artery where it is distributed to the many branches (arterioles, capillaries) that supply the tumor T with blood. If the embolic material EM comprises a radiopaque or echogenic material, the tumor T may be fluoroscopically or ultrasonically imaged to confirm that the vessel network VN is filled with the embolic material EM.

Figure 3E:
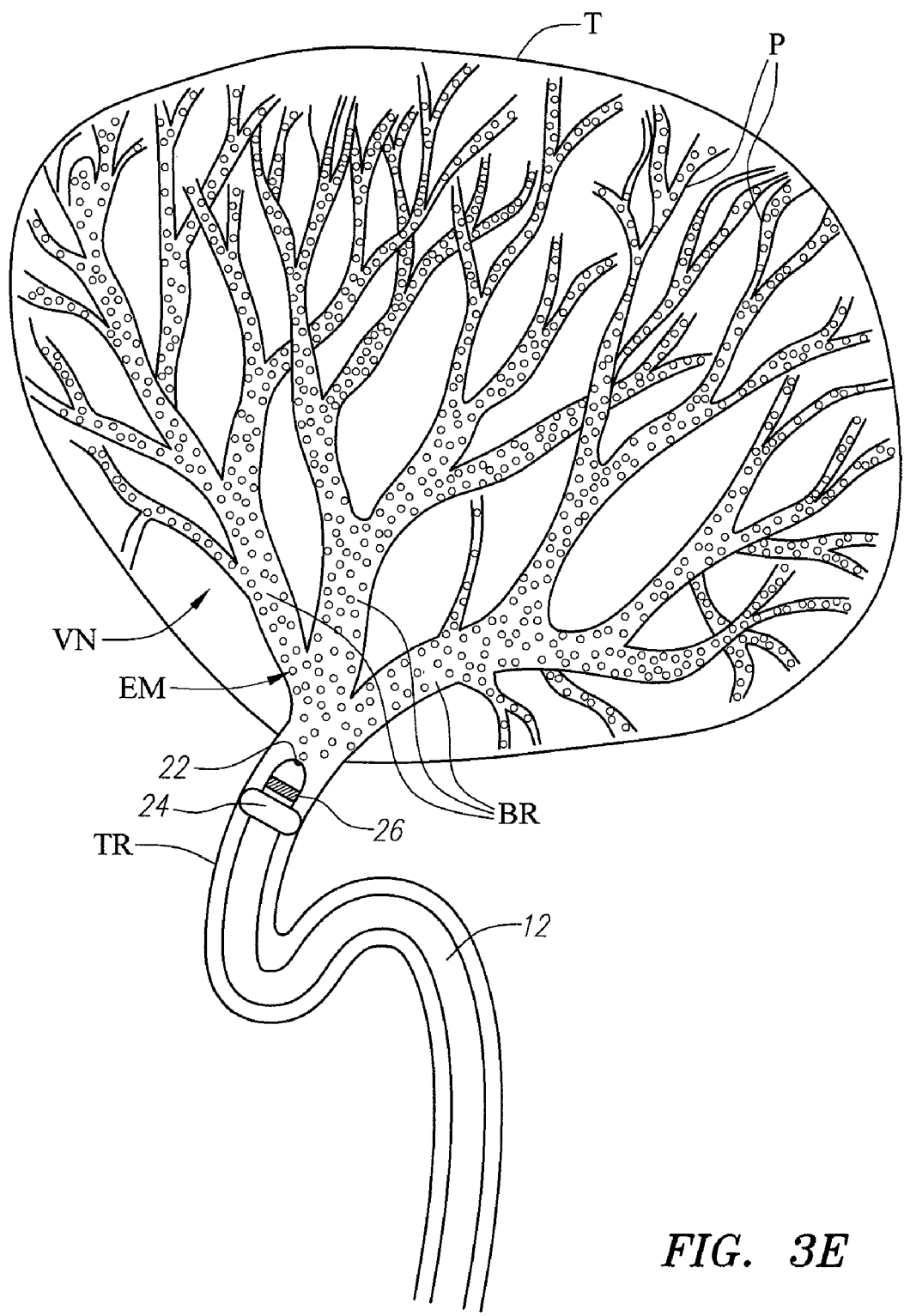

Next, the inflation medium is delivered from the source 16 (shown in FIG. 1) through the catheter 12 and into the interior of the balloon 24 to inflate it, thereby containing and stabilizing the embolic material EM within the vessel network VN (FIG. 3E). In alternative methods, rather than expanding a balloon 24, other containments mechanisms, such as those previously discussed above, can be delivered from the catheter 12 into the vascular network VN. In the case where the embolic material is self-stabilizing, e.g., if the embolic material is configured to quickly harden in response to environmental conditions, expansion of a balloon 24 or the use of any containment mechanism may not be necessary.

In any event, the stabilized embolic material EM assumes the geometry of the vessel network VN to form a vascular electrode array. As can be seen, the portion of the vascular electrode array corresponding to the trunk T of the vessel network VN can be considered the shaft of the electrode array, and the portions of the vascular electrode array corresponding to the vessel branches BR and peripheral vessels P of the vessel network VN can be considered the tines of the electrode array. In the preferred method, the embolic material EM hardens, e.g., naturally over a period of time or in response to the pH of the blood or increased temperature within the vessel network VN. In this manner, the embolic material EM resists closure of the lumens of the vessel network VN, which may otherwise occur during subsequent ablation of the tumor T.

Figure 3F:
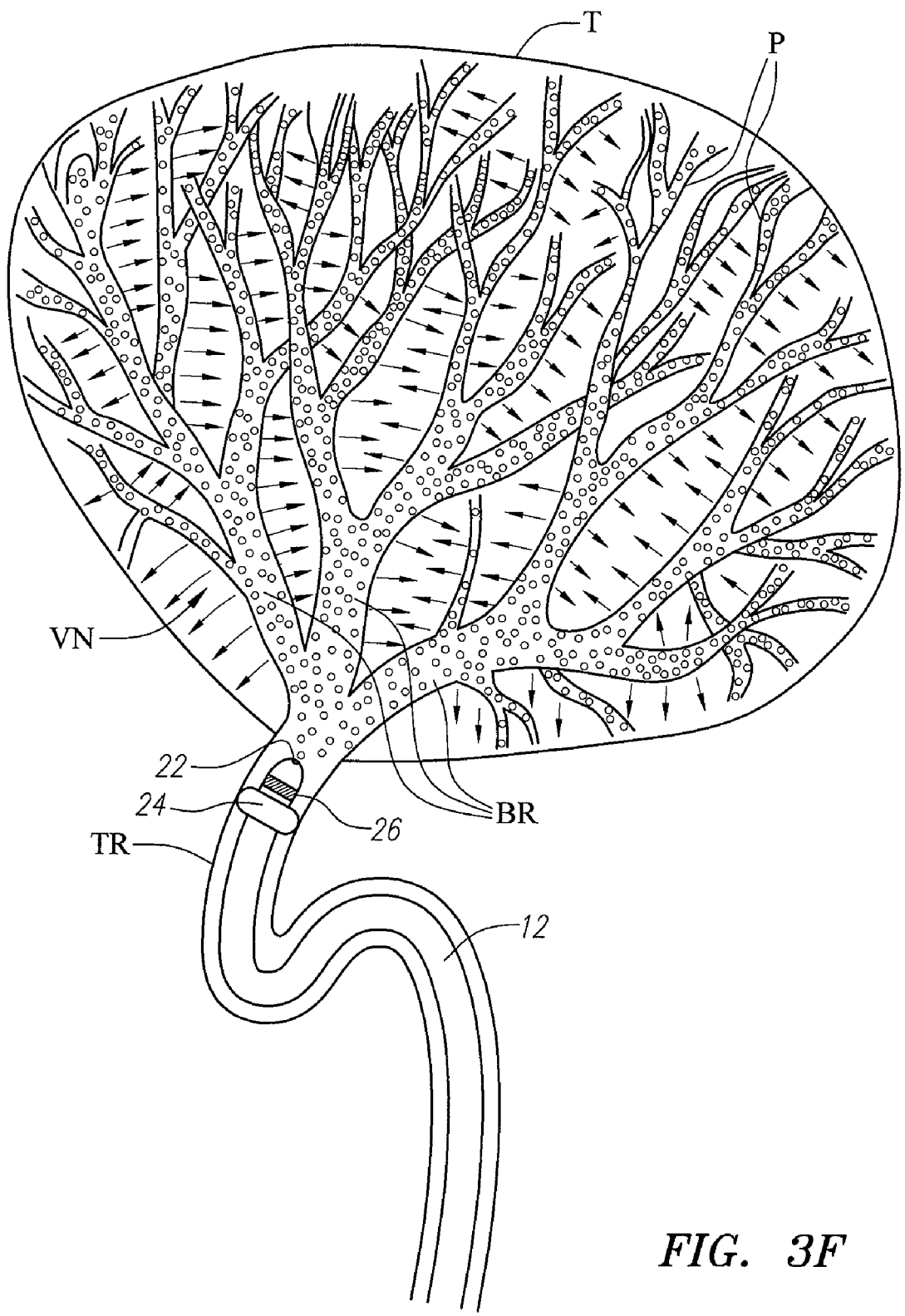

While the electrode 26 is in contact with the vascular electrode array, RF energy is conveyed from the RF generator 18 (shown in FIG. 1) through the catheter 12 to the electrode 26 (FIG. 3F). The RF energy (shown as arrows) is in turn conveyed from the electrode 26 through the vascular electrode array and into the surrounding tumor T, thereby ablating the tumor T. Alternatively, the electrode 26 may not be in contact with the vascular electrode array when the RF energy is conveyed from the RF generator 18. In this case, because of the electrical conductivity of the tissue, and through inductance, the vascular electrode array is indirectly exposed to the RF energy conveyed from the electrode 26 of the catheter 12. In either case, RF energy will be distributed throughout the tumor T to ablate a greater region than what would be ablated with just the electrode 26. Notably, because the vascular electrode array is hard, the vessel network VN will not close, so that no break is created in the conductive pathway within the vascular electrode array, so RF energy continues to flow through the tines of the vascular electrode array though the treatment.

In the illustrated method, the entirety of the tumor T is ablated, since the vascular electrode array extends through the entirety of the tumor T. Alternatively, a region of the tumor T may be ablated at one time by forming the vascular electrode array within only a region of the vessel network VN, which when activated, ablates the corresponding region of the tumor T.

After the initial treatment, the inflation medium is removed from the balloon 24, e.g., by applying a vacuum to the inflation port 32, which causes the balloon 24 to deflate, and the catheter 12 is then removed from the patient. If the vascular electrode array is non-resorbable, subsequent follow-up treatments can be perform by reapplying RF energy to the vascular electrode array to ablate any remaining portion of the tumor T or ablate any portion of the tumor T that has grown since the initial treatment.

Referring to FIGS. 4A-4D, a method of treating a tumor with the tissue treatment kit 50 illustrated in FIG. 2 will now be described. The main differences between this method and the method illustrated with respect to FIGS. 3A-3F is the tumor in this method will be treated using three separate probes that are directly introduced into the patient's body, whereas a single probe was intravascularly introduced into the patient's body in the previous method.

Figure 4A:
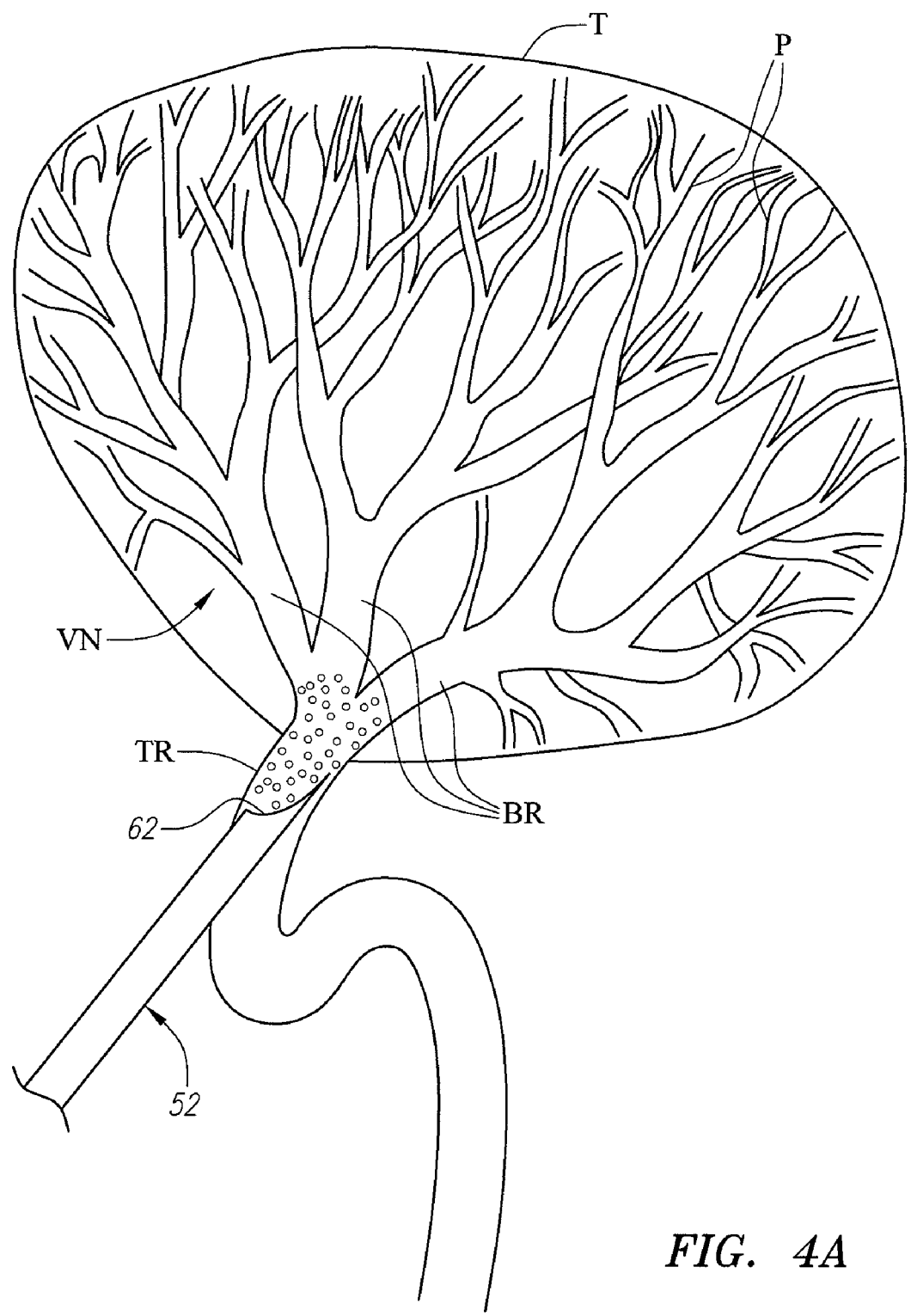
FIGS. 4A-4D illustrate views of one preferred method of using the tissue treatment kit of FIG. 2 to treat a vascularized tumor.
Figure 4B:
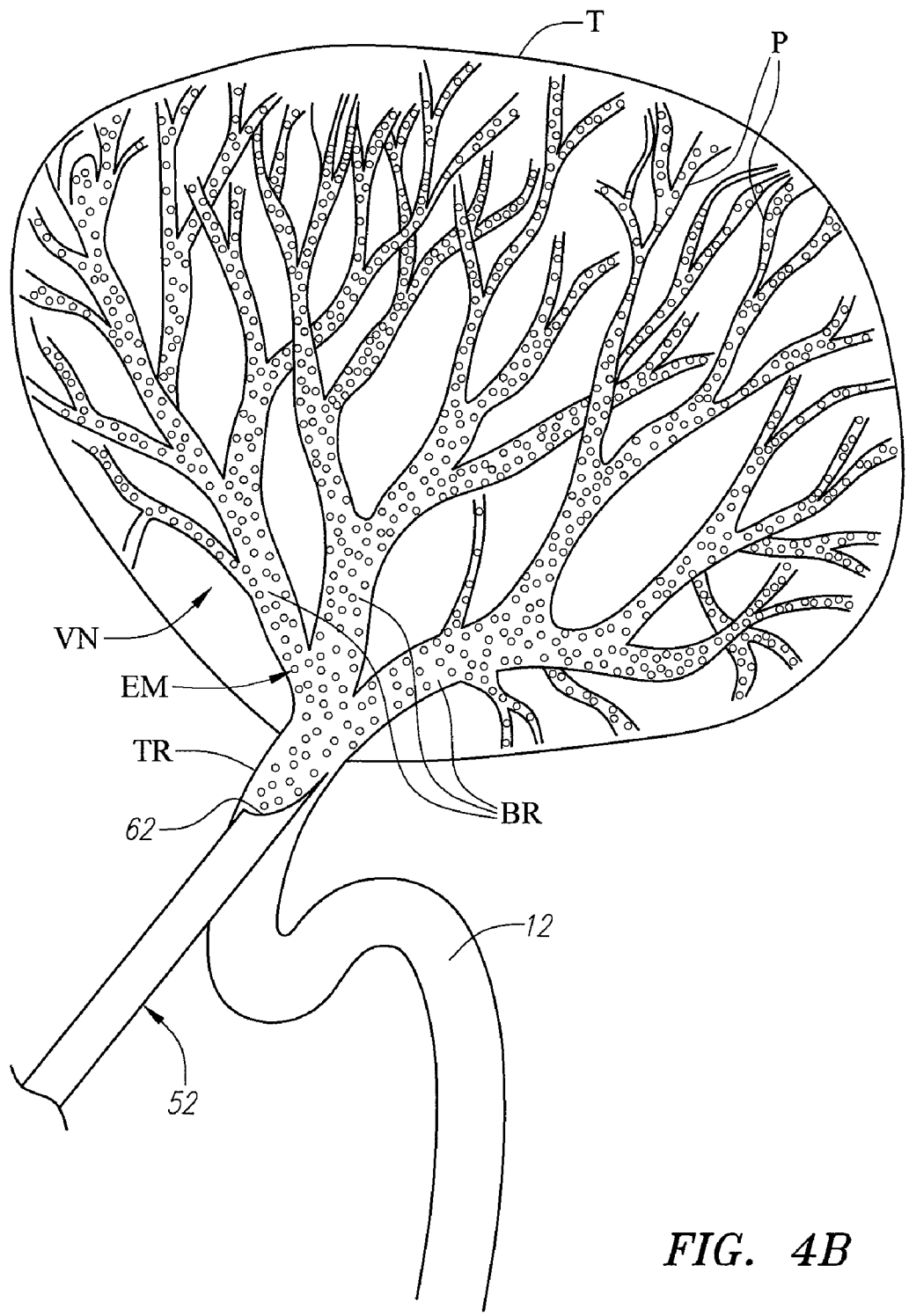

First, the embolic material delivery probe 52 is directly introduced through the patient's skin or through an open surgical incision until the distal end of the probe 52 resides within the trunk TR of the vessel network VN, and the electrically conductive embolic material EM is delivered from the embolic material source 14 (shown in FIG. 1) through the probe 52 and out of the delivery port 62 into the trunk TR of the vessel network VN, where it is conveyed into the vessel branches BR and smaller peripheral vessels P (FIG. 4A). In the same manner described above, the solid particles suspended within the solution of the embolic material EM will flow into and lodge within the smaller peripheral vessels P, thereby allowing proximal branch BR vessels and trunk T to fill with the embolic material EM (FIG. 4B).

Figure 4C:
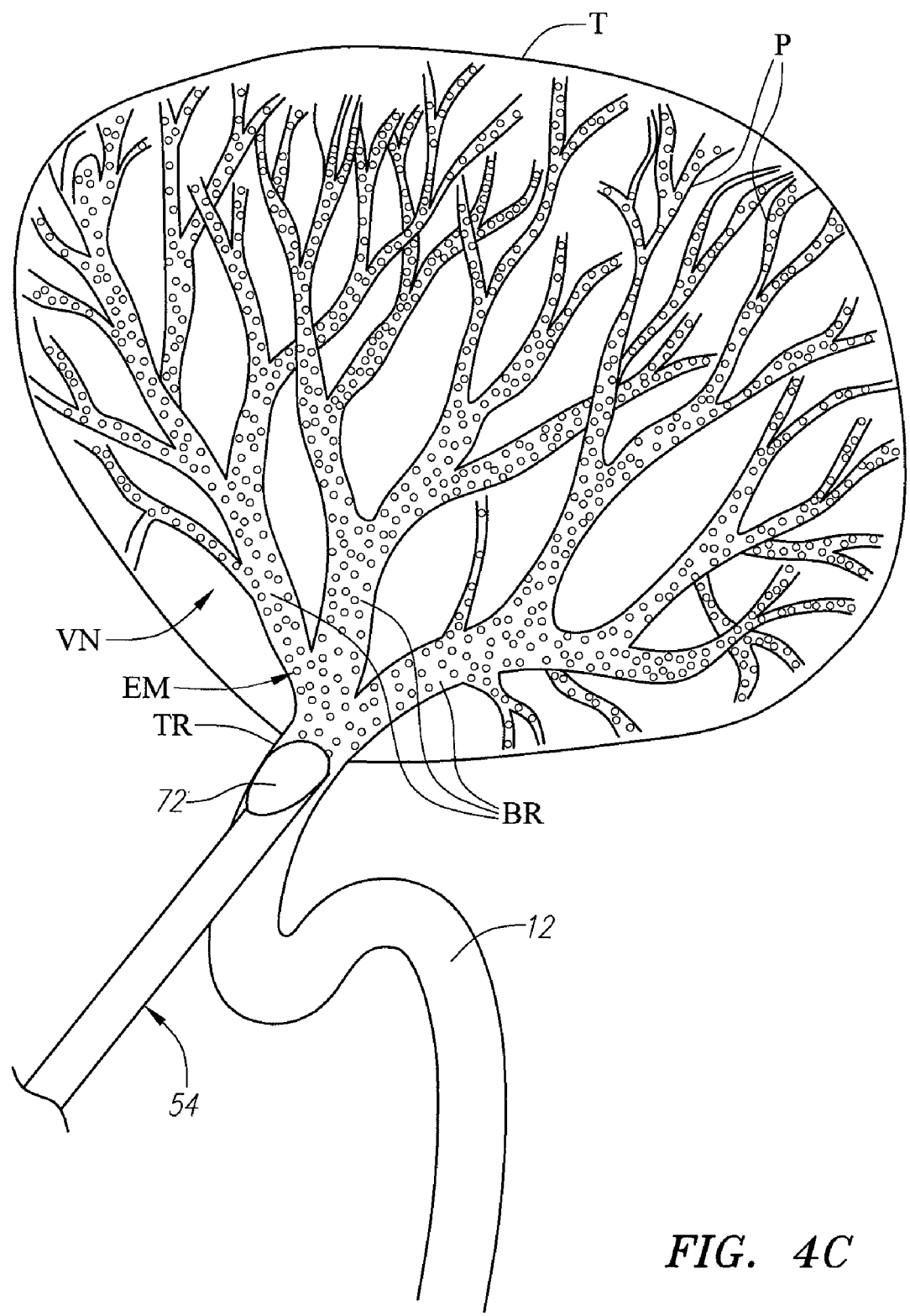

Next, the embolic material delivery probe 52 is removed from the patient. The vessel occlusion probe 54 is then directly introduced through the patient's skin or through an open surgical incision until the distal end of the probe 54 resides within the trunk TR of the vessel network VN, and inflation medium is delivered from the source 16 (shown in FIG. 1) through the probe 54 and into the interior of the balloon 72 to inflate it, thereby containing and stabilizing the embolic material EM within the vessel network VN (FIG. 4C). Alternatively, other vessel occlusive agents can be introduced into the trunk TR of the vessel network VN. Once the embolic material EM has been fully stabilized, the balloon 72 is deflated by removing inflation medium out of the inflation medium entry port 76, and the probe 54 is removed from the patient.

Figure 4D:
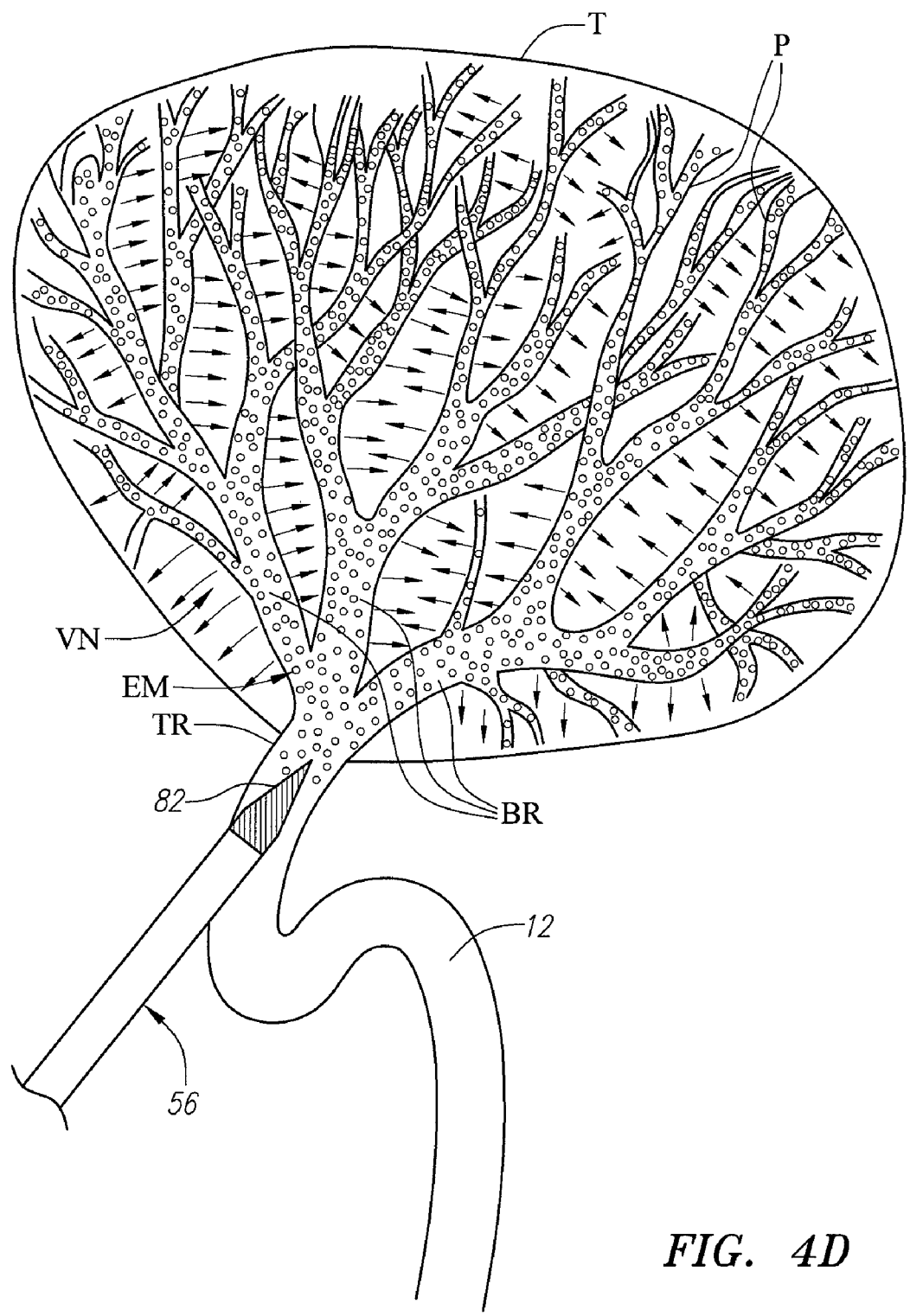

The tissue ablation probe 56 is then directly introduced through the patient's skin or through an open surgical incision until the electrode 82 on the probe 56 is in contact with the vascular electrode array, and RF energy is conveyed from the RF generator 18 (shown in FIG. 1) through the probe 56 to the electrode 82 (FIG. 4D). The RF energy (shown as arrows) is in turn conveyed from the electrode 26 through the vascular electrode array and into the surrounding tumor T, thereby ablating the tumor T. Alternatively, as previously described above, the electrode 82 may not be in contact with the vascular electrode array when the RF energy is conveyed from the RF generator 18, but instead indirectly exposes the vascular electrode array with RF energy via tissue conductivity and inductance. Once treatment is complete (whether or not subsequent treatment is needed), the tissue ablation probe 56 is removed from the patient.

In the method illustrated in FIGS. 4A-4D, the probes 52, 54, and 56 may be introduced through the same opening in which the embolic material delivery probe 52 was introduced. In an optional method, a separate cannula (not shown) can be used to conveniently deliver the probes 52, 54, and 56. That is, the cannula can be initially used to access the trunk TR of the vessel network VN. While the cannula is left in place, the embolic material delivery probe 52 can then be introduced through cannula into the trunk TR, exchanged with the vessel occlusion probe 54, which can then be exchanged with the tissue ablation probe 56. Alternatively, while the illustrated method contemplates sequential delivery and operation of the probes 52, 54, and 56, two or more of the probes 52, 54, and 56 can be located in the trunk TR at the same time. For example, if containment of the embolic material must be maintained by the inflated balloon 72 of the vessel occlusion probe 54 during tissue ablation, the vessel occlusion probe 54 and tissue ablation probe 56 may be located in the trunk TR at the same time, with the electrode 82 of the tissue ablation probe 56 being distal to the inflated balloon 72. In this case, the probes 52, 54, and 56 may be introduced into the patient through different openings.

Although the methods illustrated above lend themselves well to the treatment of tissue outside of blood vessels, vascular electrode arrays may be formed within other types of vascular networks, such as the bronchial system. For example, the vascular electrode arrays may be formed in a selected portion of the bronchial system and energized to treat cancerous tissue or otherwise necrose specific portions of the lung. This procedure may be equivalent to a Lung Volume Reduction, since treated portion of the lung would not be able, after treatment, to exchange gases during respiration.

Although the methods illustrated above lend themselves well to the treatment of extravascular tissue, such as tumors, vascular electrode arrays may be formed and energized with RF energy to treat vascular ailments, such as hemorrhages as well as vascular anomalies, e.g., Arterio Vascular Malformation (AVM), Arterio Vascular Fistula (AVF), Venous Malformation (VM), and Lymphatic Malformation (LM). When RF energy is applied to the vascular electrode array, the generation of heat will shrink the collagen found in walls of small vessels (up to 3 mm in diameter) until the lumen of each vessel is fully closed. To ensure that the vessels lumens close with little or no resistance, it is important that the embolic material be of a low viscosity and applied at a low pressure. Optionally, the electrically conductive solution is not embolic at all, so that it continues to flow through the vessels that have not been fully closed, thereby allowing exposure the entire vessel network to be exposed to RF energy until closure is achieved. In this case, it is important to relatively quickly apply the RF energy to the resulting vascular electrode array before it is absorbed into the surrounding tissue. In this case, the balloon proximal to the electrode of the catheter should be inflated prior to delivery of the embolic material to help relieve pressure buildup due to blood flow, as well as to keep the embolic material from being diluted by blood. Because the electrically conductive has a low viscosity, it can be distributed through the vessel network without the aid of the blood flow.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the scope of the present inventions as defined by the claims.

The invention claimed is:

1. A method of treating targeted tissue adjacent a physiological vascular network contoured to the general shape and size of the targeted tissue, comprising:
   delivering an electrically conductive material comprising self-embolizing flowable particles within the vascular network, wherein a portion of the electrically conductive material self-embolizes in a region of the vascular network to form a continuous multi-tined vascular electrode array that assumes a geometry of the embolized region of the vascular network; and
   applying electrical energy to the vascular electrode array to therapeutically conduct electrical energy into a region of the targeted tissue adjacent the embolized region of the vascular network.

2. The method of claim 1, wherein the embolized region of the vascular network comprises the entirety of the vascular network, and the adjacent region of the targeted tissue comprises the entirety of the targeted tissue.

3. The method of claim 1, wherein the vascular network carries blood.

4. The method of claim 1, wherein the vascular network supplies blood to the targeted tissue.

5. The method of claim 1, wherein the electrically conductive material is introduced into the vascular network and the electrical energy is applied to the vascular electrode array via a single probe.

6. The method of claim 1, wherein the electrical energy is radio frequency (RF) energy.

7. The method of claim 1, wherein the adjacent region of the targeted tissue is ablated in response to the conduction of the electrical energy.

8. The method of claim 1, wherein the vascular network comprises vessels that reduce in size at a periphery of the targeted tissue, and wherein the self-embolizing particles are sized to lodge within a vessel at the periphery of the targeted tissue.

9. The method of claim 1, wherein the self-embolizing particles are doped with metallic sub-particles.

10. The method of claim 1, wherein the embolic material has a viscosity that, when the electrical energy is applied, prevents the vascular network from closing.

11. The method of claim 1, wherein the vascular electrode array comprises a main shaft from which the tines of the continuous multi-tined array extend.

12. The method of claim 1, wherein the portion of the electrically conductive material that self-embolizes is biologically non-resorbable, so that the vascular electrode array is permanent or semi-permanent, the method further comprising applying additional electrical energy to the vascular electrode array, whereby the additional electrical energy is therapeutically conducted into any anomalies in the corresponding region of targeted tissue region that have occurred after the previous application of electrical energy.

13. The method of claim 1, further comprising delivering a containment agent within the vascular network proximal to the delivered electrically conductive material to stabilize the vascular electrode array.

14. The method of claim 1, wherein the targeted tissue is a tumor.

15. A method of treating a patient, comprising:
   delivering within a vascular network an electrically conductive material comprising self-embolizing flowable particles that embolize within the vascular network, wherein a portion of the electrically conductive material embolizes in the vascular network to form a continuous multi-tined vascular electrode array that assumes a geometry of the vascular network; and applying electrical energy to the vascular electrode array to therapeutically conduct electrical energy into the vascular network.

16. A method of treating a patient, comprising:

delivering within a vascular network an electrically conductive material comprising self-embolizing flowable particles that embolize within the vascular network, wherein the electrically conductive material has a viscosity that, when introduced into the vascular network, allows the electrically conductive material to naturally flow through the vascular network;

delivering a containment agent within the vascular network proximal to the delivered electrically conductive material to stabilize the electrically conductive material, thereby forming a continuous multi-tined vascular electrode array that assumes a geometry of the vascular network; and applying electrical energy to the vascular electrode array to therapeutically conduct electrical energy into the vascular network.

* * * * *